US011224708B2

(12) United States Patent
Garbagnati

(10) Patent No.: US 11,224,708 B2
(45) Date of Patent: Jan. 18, 2022

(54) INSTRUMENT FOR ACCESSING AND VISUALIZING HOLLOW ORGANS

(71) Applicant: FONDAZIONE PER LA CURA MINI-INVASIVA TUMORI ONLUS, Pavia (IT)

(72) Inventor: Francesco Antoniomaria Garbagnati, Milan (IT)

(73) Assignee: FONDAZIONE PER LA CURA MINI-INVASIVA TUMORI ONLUS, Pavia (IT)

(*) Notice: Subject to any disclaimer, the term of this patent is extended or adjusted under 35 U.S.C. 154(b) by 237 days.

(21) Appl. No.: 16/607,136

(22) PCT Filed: Apr. 20, 2018

(86) PCT No.: PCT/IB2018/052775
§ 371 (c)(1),
(2) Date: Oct. 22, 2019

(87) PCT Pub. No.: WO2018/198005
PCT Pub. Date: Nov. 1, 2018

(65) Prior Publication Data
US 2020/0384228 A1    Dec. 10, 2020

(30) Foreign Application Priority Data
Apr. 28, 2017    (IT) .................. 102017000046337

(51) Int. Cl.
*A61M 16/04*    (2006.01)
*A61M 16/06*    (2006.01)

(52) U.S. Cl.
CPC .... *A61M 16/0495* (2014.02); *A61M 16/0463* (2013.01); *A61M 16/0465* (2013.01);
(Continued)

(58) Field of Classification Search
CPC ......... A61M 16/04–0497; A61M 2202/0466; A61M 2039/0279; A61B 1/00154; A61B 2217/005
See application file for complete search history.

(56) References Cited

U.S. PATENT DOCUMENTS 3,101,543 A * 8/1963 Baughan ................ A61C 17/08
433/94
3,768,477 A * 10/1973 Anders ................. A61C 17/08
433/91
(Continued)

FOREIGN PATENT DOCUMENTS

CN    1035948 A    10/1989
CN    101489616 A    7/2009
(Continued)

OTHER PUBLICATIONS

Office Action for Corresponding Chinese Application No. 201880028235.8, dated May 7, 2021, 8 pages, English translation 8 pages.
(Continued)

*Primary Examiner* — Rachel T Sippel
(74) *Attorney, Agent, or Firm* — Lucas & Mercanti, LLP

(57) ABSTRACT

An instrument for accessing and visualizing hollow organs is provided. The instrument includes a mouthpiece having a perforated mask and a sleeve having a generally cylindrical or ovoid shape extending from the perforated mask substantially perpendicularly thereto and defining a channel. The instrument further includes sucking means having a suction chamber or closed volume that is restrained to the mask on the side where the sleeve is formed. The suction chamber has a plurality of through openings adapted to allow fluid communication with a surrounding environment, an intake opening communicating with the suction chamber formed (Continued)

on the mask, wherein the through openings are formed on the skirt of a dome-shaped member which delimits the suction chamber.

15 Claims, 5 Drawing Sheets

(52) U.S. Cl.
CPC .... *A61M 16/0477* (2014.02); *A61M 16/0493* (2014.02); *A61M 16/0627* (2014.02); *A61M 2202/0466* (2013.01); *A61M 2205/583* (2013.01)

(56) References Cited

U.S. PATENT DOCUMENTS

| | | | |
|---|---|---|---|
| 3,928,916 A * | 12/1975 | Hansson | A61C 17/08 433/31 |
| 4,802,851 A * | 2/1989 | Rhoades | A61C 17/08 433/93 |
| 4,848,331 A | 7/1989 | Northway Meyer | |
| 6,460,540 B1 * | 10/2002 | Klepper | A61M 16/0463 128/207.14 |
| 2002/0162555 A1 | 11/2002 | West | |
| 2006/0095066 A1 | 5/2006 | Chang | |
| 2008/0011304 A1 * | 1/2008 | Stewart | A61M 16/04 128/207.15 |
| 2015/0209535 A1 * | 7/2015 | Cole | A61M 16/0463 128/202.16 |
| 2016/0256652 A1 | 9/2016 | Wiesman | |

FOREIGN PATENT DOCUMENTS

| | | |
|---|---|---|
| JP | 2008220794 A | 9/2008 |
| WO | 2014078034 A1 | 5/2014 |
| WO | 2014121199 A1 | 8/2014 |

OTHER PUBLICATIONS

International Search Report and Written Opinion for Corresponding International Application No. PCT/IB2018/052775 (13 Pages) (dated Jul. 5, 2018).

* cited by examiner

INSTRUMENT FOR ACCESSING AND VISUALIZING HOLLOW ORGANS

CROSS-REFERENCE TO RELATED APPLICATIONS

This application is a 371 of PCT/IB2018/052775, filed Apr. 20, 2018, which claims the benefit of Italian Patent Application No. 102017000046337, filed Apr. 28, 2017.

TECHNICAL FIELD OF THE INVENTION

The present invention relates in general to devices for accessing and visualizing hollow organs and in particular an instrument which can be used for guiding endoscopes in esophagus-gastro-duodenoscopy and laryngo-bronchoscopy procedures. The instrument according to the invention can also be used for the intubation and the ventilation of a patient in general anesthesia procedures performed both in the election and in the emergency regimes.

BACKGROUND

The esophagus-gastro-duodenoscopy is an instrumental examination performed by specialized doctors to diagnose, and in selected cases treat, pathologies of the upper gastroenteric tube. The examination is performed by introducing an endoscope into a patient's oral cavity and advancing its tip through the pharynx and the esophagus to reach the stomach, the duodenal bulb and the descending duodenum.

Laryngo-bronchoscopy is an instrumental examination carried out by medical specialists to diagnose, and in selected cases treat, diseases of the larynx, the trachea and the lobar bronchi and to perform cultural, cytological and/or biopsy diagnosis of inflammatory or neoplastic diseases of the tissue pulmonary. Also in this case the examination is performed by introducing an endoscope into the bronchial system through the mouth or nose of a patient.

An endoscope typically comprises a flexible tubular body coated by a sheath made of a plastic material. Endoscopes can have a diameter ranging from 4 to 10 mm and have a semi-rigid tip that is suitably bendable. Several channels that allow the introduction of vision systems, for example optical fibers, and of operative instruments, for example instruments for performing biopsies, are obtained within the flexible tubular body in the axial direction. The tubular body of the endoscope also houses appropriate tie rods that allow flexion, extension and bending of its tip. More specifically, by acting on the tie rods by means of external handpieces, a medical specialist can guide the endoscope into the various cavities that it crosses by curving and/or extending and/or rotating its tip.

As known, the introduction of an endoscope into a patient's oral cavity exposes the endoscope itself to the risk of bite damage. In fact, the patient during the endoscopic examination can unintentionally tighten the teeth and damage the sheath of the instrument. The lesion of the sheath determines the entry into the tubular body of the endoscope of liquids that irreparably damage the structures contained therein. To solve this problem a mouthpiece inserted in the patient's mouth is used. This mouthpiece comprises a mask designed to be fixed to the patient's mouth by means of a rubber band which wraps around his head. The mask is provided with a central hole from which a sleeve of generally cylindrical or ovoidal shape extends perpendicularly for a short distance, thus acting both as a guide channel and as a protection element for the endoscope, preventing the patient from biting it involuntarily.

As known, the performance of an esophagus-gastro-duodenoscopy or of a laryngo-bronchoscopy requires an adequate preparation of the patient which includes the anesthesia of the oral cavity in order to make the tongue and throat less sensitive to contact with the sheath of the endoscope. During the introduction of the endoscope and for the entire duration of the endoscopic examination, the patient is kept lying on a bed and generally lying on the left side to allow the exit from his mouth of saliva and any other liquids drained into the oral cavity from the esophagus, which are typically collected on an absorbent cloth or manually aspirated with a suction tube.

Despite these measures, the esophagus-gastro-duodenoscopy and laryngo-bronchoscopy are invasive examinations which are rather annoying for a patient, when introducing the endoscope into the oral cavity, when advancing the instrument in the hollow organs to be inspected and when sampling tissue samples.

Said annoyance derives essentially from two factors. On one side there is the rubbing of the endoscope sheath during the repeated movements of its advancement and retraction on the lower wall of the hard palate, on the front wall of the soft palate and on the rear wall of the pharynx. On the other hand there is the profuse salivation that induces in the patient the involuntary reflex of swallowing, which is however hindered and made impossible by the presence of the endoscope. This results in the feeling of nausea and retching and the unwanted ab-ingestis which induces persistent cough and a sense of suffocation.

Tracheal intubation for performing general anesthesia is carried out by means of positions of a dedicated tube, equipped with a tracheal anchor balloon, during direct or indirect visualization of the larynx obtained by lowering and moving the tongue with a rigid blade laryngoscope (possibly equipped with combined visual systems) in a patient lying supine and in forced hyperextension of the cervical spine. In cases of difficult intubation (for example in large obese, in patients with anatomical abnormalities, etc.), the tube dedicated to the anesthesia can be inserted using a normal flexible laryngoscope as a guide mandrel.

The common problems related to the use of rigid laryngoscopes are related to the traumatism due to their introduction into the oral cavity, which, having to be rapid due to the apnea induced by the drugs administered in the induction phase of the anesthesia, determines trauma and damage of the lips, tongue, teeth, gums and vocal cords which result in permanent damage causing civil or criminal cases with a claim for compensations. The risk of non-intubation in the induction phase of anesthesia can cause severe and persistent hypoxia with possible neurological and even fatal damage. In cases of difficult intubation, the use of the flexible laryngoscope requires a programmed displacement to an operating room of an endoscopic column, which is expensive and not always available, and the use of a non-dedicated optical vision system that requires sterilization.

WO 2014/121199 A1 and U.S. Pat. No. 4,848,331 describe instruments according to the preamble of claim 1. These instruments comprise a suction chamber provided with through openings arranged on the side opposite to the mask, i.e. facing the patient's larynx, so that the suction chamber can suck a relatively reduced amount of saliva and there is the risk of aspiring the velum instead.

SUMMARY OF THE INVENTION

The technical problems posed and solved by the present invention are therefore those of providing an instrument for accessing vision to hollow organs which allows to overcome the above mentioned disadvantages with reference at the state of the art. These problems are solved by an instrument according to claim 1.

Preferred features of the present invention are the subject of the dependent claims.

The instrument according to the invention for accessing and visualizing hollow organs comprises a mouthpiece configured to be inserted in the mouth of a patient and equipped with means for allowing the aspiration of saliva and other fluids present in the oral cavity. Such suction means are made as a chamber, or closed volume, arranged on the side of the mask intended to be directed towards the patient's mouth. The suction chamber is then introduced into use in the oral cavity of a patient.

The suction chamber is preferably made coaxially to the mouthpiece sleeve and comprises a plurality of holes for communication with the patient's oral cavity. A further hole is obtained in the mask on the side facing the operator and serves to put the suction chamber in communication with the outside in order to create a connection with a suction tube.

The instrument for accessing and visualizing hollow bodies may further comprise a flexible tubular element which can be inserted into the mouthpiece sleeve. The flexible tubular element extends beyond the sleeve for a length such that, in an operative configuration of the instrument, its distal end is positioned beyond the patient's cricopharyngeal ring in the case of an esophagus-gastro-duodenoscopy, or in the trachea beyond the vocal cords in the case of a bronchoscopy or tracheal access in the induction phase of general anesthesia.

The flexible tubular element, in all cases forms a curved channel that allows the introduction of an endoscope, a suction system or other operating instruments in the member in which its distal end is positioned.

The flexible tubular element it is provided with a locking system at its proximal end which allows to attach it to the mouthpiece when its distal end has been correctly positioned in the esophagus or trachea. According to a preferred embodiment of the invention, the flexible tubular element is removably inserted into the sleeve of the mouthpiece, thus allowing to simplify the structure of the individual components and to use interchangeable flexible tubular elements of different lengths according to age, sex, the size of the oral cavity and the anatomical conformation of the patient.

Advantageously, the flexible tubular element can be provided with a radially expandable distal portion, for example a balloon, which allows it to be anchored to the trachea, thus allowing direct use of the instrument for intubation of a patient. The balloon expandable portion at the distal end of the tubular member can be inflated through a channel of communication with the exterior included in the wall of the tubular element itself. By connecting a respirator to the proximal part of the tubular element anchored to the mouthpiece it is thus possible to ventilate a patient. This feature of the invention allows the use of the instrument for accessing and visualizing hollow organs not only for endoscopic examinations such as the esophagus-gastro-duoudenoscopy and the laryngo-bronchoscopy, but also for the intubation of a patient in general anesthesia procedures instead of the currently used rigid instruments.

The flexible tubular element can include in its wall a vision system, for example with optic fibers, which allows continuous vision of both the trachea, throughout the duration of a surgical operation conducted under general anesthesia, and of the proximal esophagus during the execution of endoscopies of the upper tract of the digestive system.

The flexible tubular element can include in its wall an operative channel that allows the suction of bronchial secretions during the procedures of total anesthesia.

Furthermore, the instrument for accessing and visualizing hollow organs may comprise a tubular introducing mandrel configured to be removably inserted into the flexible tubular element. The introducing mandrel comprises suitable tie rods operable by external handpieces, with which an operator can flex or extend its tip to guide the tubular element into the esophagus, trachea or stomach. The introducing mandrel is provided with a vision system, for example an optical fiber system. This offers the advantage of allowing visualization of the patient's oral cavity and of the cavities of interest during the positioning of the flexible tubular element of the instrument. The introducing mandrel also has a blunted and rounded tip made of soft and non-traumatic material.

According to an embodiment of the invention, the mouthpiece of the instrument for accessing and visualizing hollow organs can advantageously comprise first and second sleeves and first and second flexible tubular elements, wherein one of the flexible tubular elements comprises a radially expandable portion, for example balloon-shaped, adapted to permit its locking in a patient's trachea. This configuration of the instrument according to the invention allows the performance of real surgical operations under general anesthesia, because the patient can be ventilated through the flexible tubular element that can be inserted and blocked in the trachea and at the same time endoscopes and surgical instruments can be introduced into the digestive tract through the other flexible tubular element.

According to an embodiment of the invention, the instrument for accessing and visualizing hollow organs can advantageously comprise a flexible guide made of plastic material configured to be inserted into the flexible tubular element and having a length suitable to reach the inside of a patient's stomach or bronchi. The flexible guide includes a plurality of lumens obtained in the axial direction, which allow the introduction of endoscopes and surgical instruments for the performance of biopsies and actual interventions for the removal of polyps, tumors and the like, while minimizing discomfort and pain borne by the patient. The flexible guide, in fact, forms a fixed channel through which it is possible to guide and move endoscopes and surgical instruments.

Thanks to this combination of features, the instrument for accessing and visualizing hollow organs according to the invention allows to drastically reduce discomfort, pain, feeling of nausea and vomiting borne by a patient while performing an esophagus-gastro-duodenoscopy or a bronchoscopy.

In fact, thanks to the presence of the suction chamber, saliva and other fluids are aspirated for the whole duration of the examination, thereby avoiding the onset of coughing and choking sensation experienced by the patient and minimizing the feeling of nausea and vomiting due to the reflection of swallowing made impossible by the presence of the endoscope in the esophagus.

The positioning of the flexible tubular element in the initial tract of the esophagus or trachea in a fixed position relative to the oral cavity of the patient eliminates the rubbing of the endoscope on the pharyngeal mucosa due to repeated movements of advancement and retraction during a procedure, thereby further reducing the feeling of nausea and vomiting as well as the feeling of thrust and pain due to the microtrauma from rubbing caused by the instrument on the pharynx. In addition, the beveled shape of the mandrel tip provided with a visual system allows to reduce the risk of perforation of the esophagus and to avoid entry into esophageal diverticula.

When the instrument according to the invention for accessing and visualizing hollow organs is used for general anesthesia procedures, the advantages are quite evident. Selective intubation of the trachea by inserting the mandrel equipped with a visual system through the mouthpiece sleeve avoids the traumatism caused by rigid laryngoscopes on the structures of the mouth and the oral cavity (lips, tongue, gums, teeth and palate) as well as those of the pharynx (velum) and larynx (vocal cords). The introduction in direct vision allows to perform with precision and determine with certainty the correct access to the trachea, thereby avoiding the possibility of prolonged hypoxia related to the difficulty of intubation with a rigid laryngoscope of traditional type and, which is fundamental, allows the induction of respiratory paralysis by means of curare or the like after placing the tracheal access in a certain and definitive way. The certainty of correct positioning is visual and direct, so that the stethoscope, with the known problems related to its use, such as difficulties in obese patients, anesthetist's auditory problems, etc. is not necessary.

In addition to the aforementioned advantages, with respect to the use of flexible laryngoscopes as mandrels for guiding an anesthesia tube, the instrument according to the invention has the advantage of not requiring the use of endoscopic columns in the operating room, especially in emergency procedures performed outside an operating room. Furthermore, it is not necessary to sterilize the endoscope as it is supplied sterile. Another advantage is that the flexible tubular element bound to the mouthpiece allows continuous vision of the trachea and lobar bronchi during an operation and the possible targeted aspiration of the bronchial secretions. A further advantage offered by the invention is that the instrument for accessing and visualizing hollow organs is in principle structurally simpler and less expensive than the endoscopy instruments currently available. Other advantages, features and methods of use of the present invention will become evident from the following detailed description of some embodiments thereof, presented for illustrative and non-limiting purposes.

BRIEF DESCRIPTION OF THE FIGURES

Reference will be made to the figures of the accompanying drawings, in which.

DETAILED DESCRIPTION OF PREFERRED EMBODIMENTS

Figure 1:
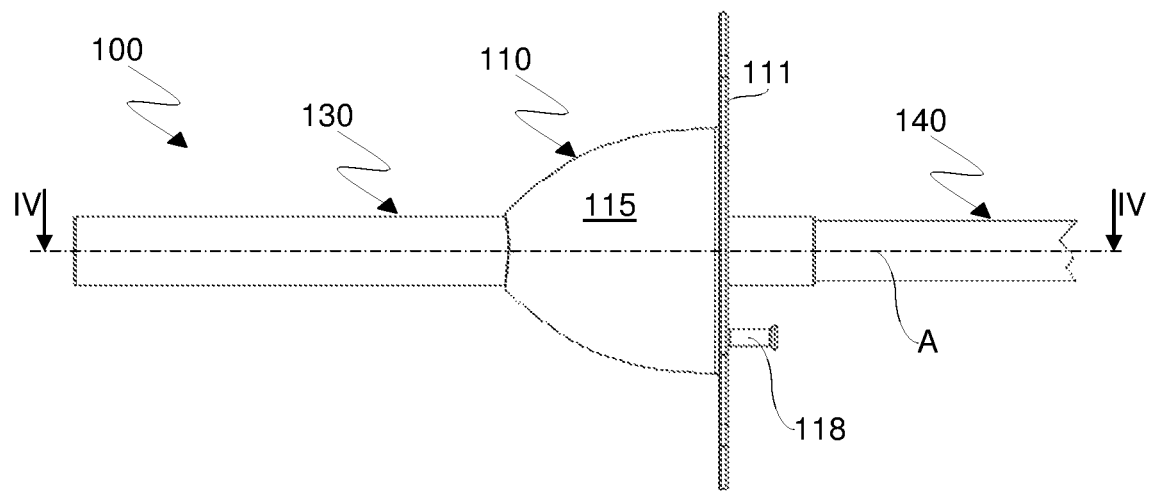
FIGS. 1 to 3 are respectively a top plan view, a side view and a rear view of an instrument for accessing and visualizing hollow organs according to the invention.

With reference initially to FIGS. 1 to 5, an instrument for accessing and visualizing hollow organs according to the invention is generally indicated by reference numeral 100.

Instrument 100 comprises a mouthpiece 110 configured to be inserted into a patient's mouth. The mouthpiece 110 comprises, in a known manner, a mask 111 which is perforated, for example in the center, and a sleeve 112 having a generally cylindrical shape and a circular or elliptical cross-section which extends from the hole formed in the mask 111 in a direction substantially perpendicular to it, thereby defining a channel suitable for allowing the introduction of a flexible tubular element. The mask 111 also comprises in a known manner a pair of through openings 113, 114, for example of circular shape, obtained at its opposite ends with respect to an axis A of the sleeve 112 and configured to allow the assembly of a band (not shown) which is elastic or of another suitable material for maintaining the mask 111 permanently in position once the mouthpiece 110 has been inserted into the mouth of a patient.

According to the invention, the mouthpiece 110 further comprises means for aspirating saliva and other fluids from the oral cavity of the patient. Such suction means are realized as a suction chamber 120, or closed volume, arranged on the side of the mask 111 intended to be facing the mouth of the patient, i.e. the side on which the sleeve 112 is formed. For reasons of space the suction chamber 120 is preferably made coaxially to the sleeve 112 of the mouthpiece 110 and is delimited by a dome-shaped member 115 having a base connected to the mask 111 and a top connected to the free end of the sleeve 112 itself, which mouths at the latter.

One or more through openings 116 are provided on the skirt of the dome-shaped member 115 for placing the chamber 120 in fluid communication with the surrounding environment. In an operating condition of the instrument 100, the surrounding environment is in particular the oral cavity of a patient.

Preferably, at least two through openings 116, in particular three pairs of through openings 116, are arranged on the dome-shaped member 115 in opposite positions with respect to the sleeve 112. The dome-shaped member 115 has in particular substantially elliptical cross-sections which become larger toward the mask 111. The through openings 116 are preferably arranged along major axes of substantially elliptical cross-sections of the dome-shaped member 115.

A through opening 117 is provided on the mask 111 to allow the connection of an aspirator (not shown) to the chamber 120 of the mouthpiece 110. It will therefore be understood that in an operating condition of the instrument 100 the aforementioned configuration of the suction chamber 120 allows the collection and elimination of fluids from the oral cavity of a patient. In the embodiment of the invention shown in the figures, the through opening 117 is formed on the top of a column 118 formed on the face of the mask 111 intended to be facing outwards, i.e. the face opposite to the one where the chamber 120 is located. This configuration facilitates the mounting of the aspirator.

The instrument 100 for accessing and visualizing hollow members further comprises a flexible tubular element 130 inserted or insertable into the sleeve 112. The flexible tubular element 130 is made of a flexible plastic material and its perimeter wall may be advantageously reinforced with metal elements such as a helical spring.

A distal end of the flexible tubular member 130 protrudes for a distance beyond the distal end of the sleeve 112, i.e. the free end opposite to the end joined to the mask 111, and has the function of a fixed guide which, in use, is arranged according to a slightly curved configuration in the patient's oral cavity, for example between the pharynx and the esophagus in the case of an esophagus-gastro-duodenoscopy, or between the pharynx and the larynx in the case of a laryngo-bronchoscopy.

The flexible tubular element 130 has a length such that, in an operating configuration of the instrument for accessing and visualizing hollow organs 100, its distal end is positioned beyond the cricopharyngeal ring of a patient in the case of an esophagus-gastro-duodenoscopy, or beyond the vocal cords in the case of a laryngo-bronchoscopy.

The flexible tubular element 130 allows the passage and maneuvers of advancing and retracting a traditional endoscope without the latter coming into contact with the walls of the cavity oral and pharynx, thereby reducing the secondary traumatism and thus helping to reduce the discomfort borne by the patient in synergy with the suction chamber 120 associated with the mouthpiece 110.

According to a preferred embodiment of the invention, the flexible tubular element 130 is inserted in a removable manner into the sleeve 112 of the mouthpiece 110. For this purpose, the flexible tubular element 130 and the mask 111 comprise connecting means of complementary shape, for example in the form of at least one radial projection 131 formed on the perimeter wall of the tubular element 130 and of a seat 119 having a corresponding shape formed in the mask 111 at the inlet of the sleeve. In the illustrated embodiment, for example, two diametrically opposite projections 131 are shown. According to a preferred embodiment of the invention, the connecting means between the flexible tubular element 130 and the mask 111 define a snap lock, thus making the coupling stable and offering a user a tactile and audible feedback to confirm the assembly occurred between the two parts. The connecting means may also be in the form of magnets.

Figure 2:
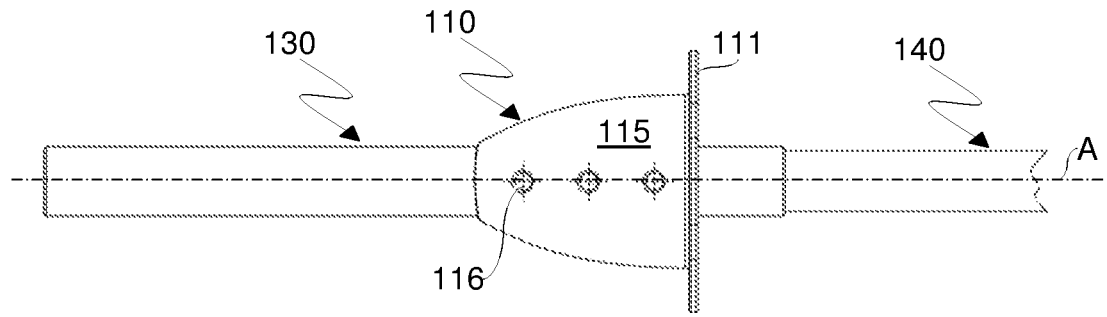
Figure 3:
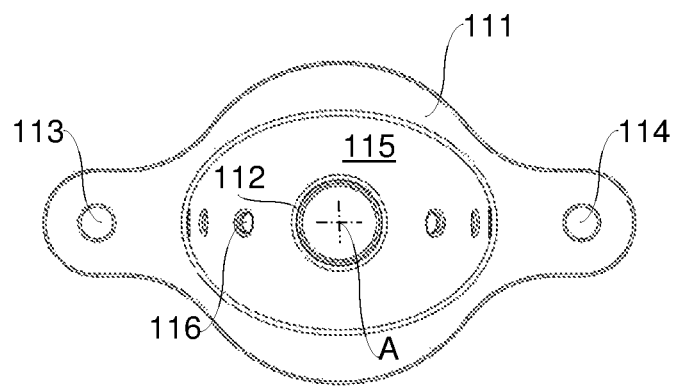
Figure 4:
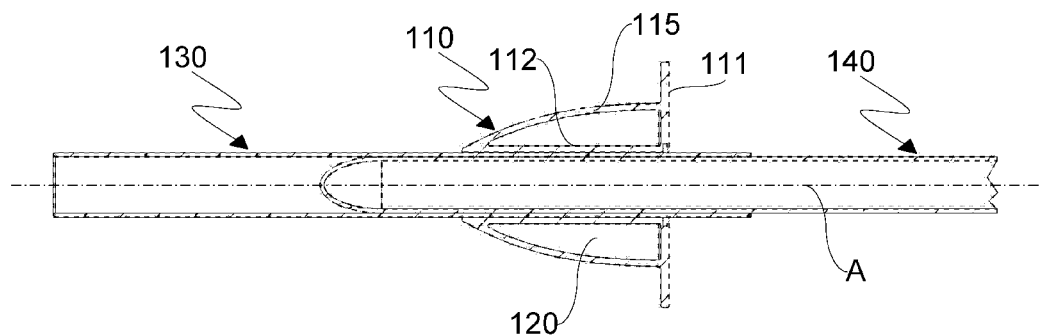
FIG. 4 is a longitudinal sectional view of the instrument for accessing and visualizing hollow organs taken along a plane passing through the line Iv-Iv of FIG. 1.
Figure 5:
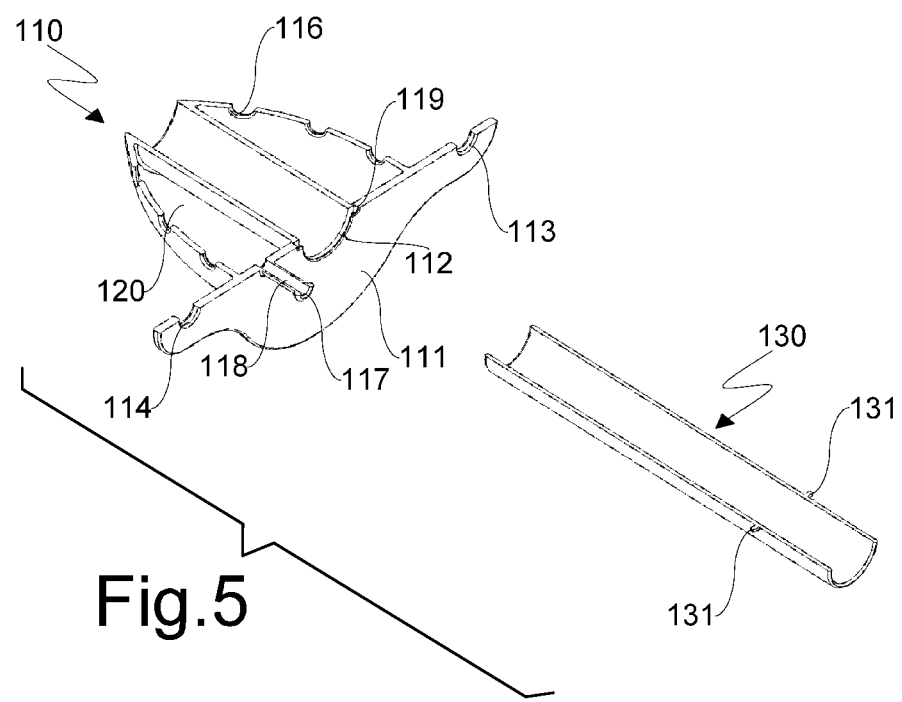
FIG. 5 is a perspective exploded view and in longitudinal section of the instrument for accessing and visualizing hollow organs according to the invention without the introducing mandrel.

The instrument 100 for accessing and visualizing hollow organs according to the invention further comprises an introducing mandrel 140, which is removably inserted into the tubular element 130 during the introduction and the positioning of the instrument 100 itself in the oral cavity of a patient and subsequently retracted to allow access through the tubular element 130. In FIGS. 1, 2 and 4 the introducing mandrel 140 is shown partially in section and inserted up to approximately the middle of the tubular element 130. In an operative configuration of the instrument 100, the distal end of the introducing mandrel 140 protrudes for a distance beyond the distal end of the tubular element 130, thus allowing its guidance and positioning in the oral cavity, esophagus or trachea of a patient.

The introducing mandrel 140 comprises tie rods associated with respective handpieces (both not shown) that allow its flexion and extension to adapt to the curvature of the cavities progressively crossed. The introducing mandrel 140 further comprises a vision system (not shown), for example an optical fiber system, associated with its distal end, which facilitates its guiding in the oral cavity and therefore favors the positioning of the instrument 100 for accessing and visualizing hollow organs.

According to a variant embodiment of the invention, the tubular element 130 can itself act as an introducing mandrel. For this purpose, it may be provided with tie rods associated with respective handpieces which allow flexion and extension to adapt to the curvature of progressively crossed cavities, as well as a removable core adapted to allow access to the tracheal lumen.

During the positioning of the instrument 100, the mask 111 abuts against the patient's lips acting as a stop element and is locked in this position by the elastic band, or other material suitable for the purpose, mounted in the through openings 113 and 114. The suction chamber 120 is thus positioned in the patient's oral cavity to allow the aspiration of saliva and other fluids during the performance of an esophagus-gastro-duodenoscopy or of a laryngo-bronchoscopy, and, in synergy with the sleeve 112, at the same time performs the function of protective element to prevent the patient from clamping the teeth against the sheath of an endoscope.

The distal end of the flexible tubular element 130 is instead inserted into the patient's esophagus or trachea according to the examination that must be performed. The suction chamber 120 and the initial portion of the flexible tubular element 130 also allow to keep the patient's tongue in a natural and fixed position.

The flexible tubular element 130 can advantageously be provided with a vision system, for example with optical fibers, inserted or insertable in a through channel obtained in its wall that leads to the distal end. The provision of a vision system is advantageous because it allows the vision of the patient's cavities even once the introducing mandrel 140 has been removed.

Figure 6:
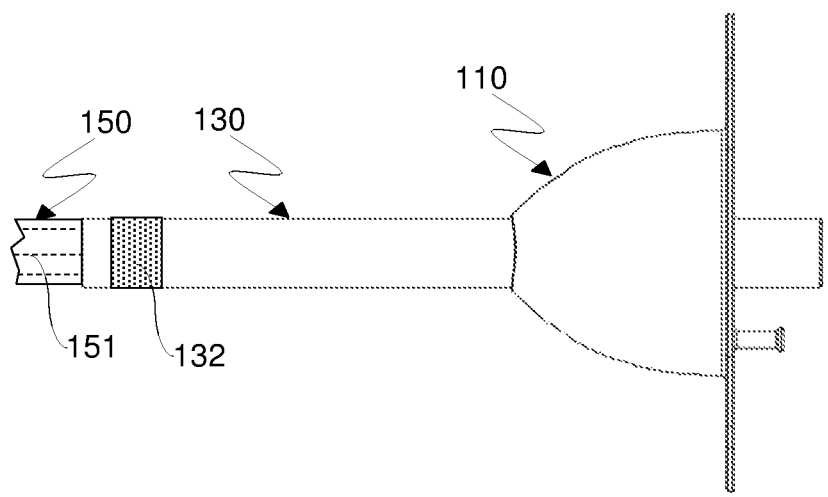
FIGS. 6 and 7 are, respectively, a top plan view and a side view of an instrument for accessing and visualizing hollow organs according to a variant of the invention.
Figure 7:
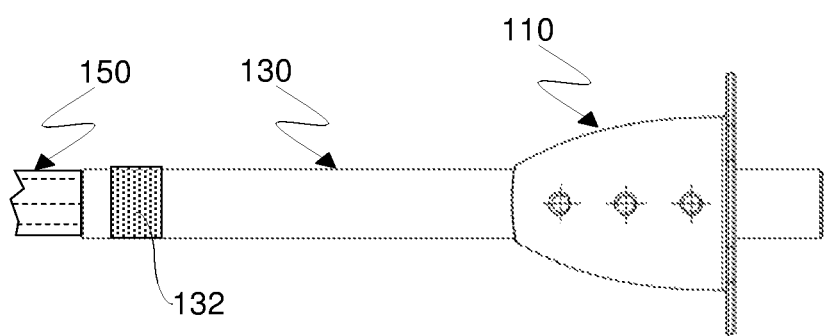

Referring now to FIGS. 6 and 7, according to an embodiment of the invention, the instrument 100 for accessing and visualizing hollow organs can also include a flexible guide 150 configured to be inserted into the flexible tubular member 130 once the introducing mandrel 140 has been removed. The length of the flexible guide 150 is greater than the length of the flexible tubular member 130 and may for example be suitable to allow reaching a patient's stomach or his bronchial system.

The flexible guide 150 comprises a plurality of lumens of various lengths 151 obtained in the axial direction, which allow the introduction of endoscopes, suction tubes, injection tubes of liquids and other surgical instruments for performing biopsies, surgical interventions for removing polyps or tumors and other operating procedures. In FIGS. 6 and 7 these lumens are schematically indicated with dashed lines. It will be understood that the flexible guide 150 constitutes an extension of the flexible tubular element 130, offering the same advantages in terms of guide and protection of the endoscopes and consequent reduction of discomfort and pain for the patient.

According to a further aspect of the invention, the flexible tubular element 130 may be provided with a radially expandable distal portion, for example in the form of a balloon, by insufflation of gases or liquids through a suitable channel formed in its perimeter wall. The distal expandable portion 132 is configured to be hermetically locked in the trachea of a patient, thereby allowing his ventilation upon connection of a breathing apparatus to the proximal end of the tubular member 130 fixed to the mouthpiece 110. The instrument 100 according to the invention can thus be advantageously used not only for endoscopy procedures, but also for intubation and ventilation in general anesthesia procedures carried out in an elective or urgent procedure as exemplified in FIGS. 6 and 7.

Figure 8:
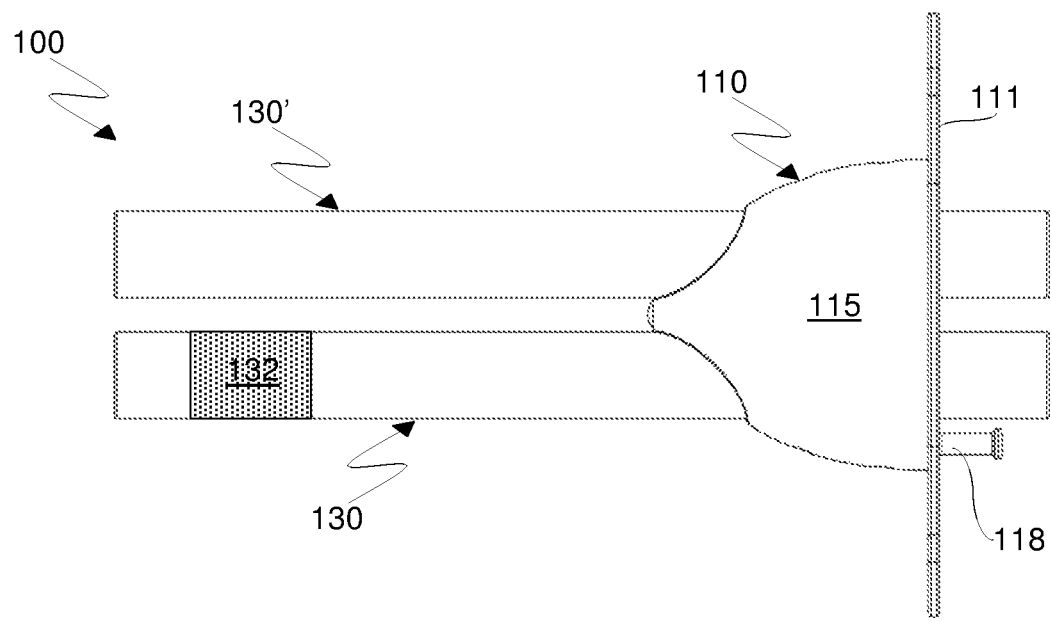
FIGS. 8 and 9 are respectively a top plan view and a side view of an instrument for accessing and visualizing hollow organs according to a further variant of the invention.
Figure 9:
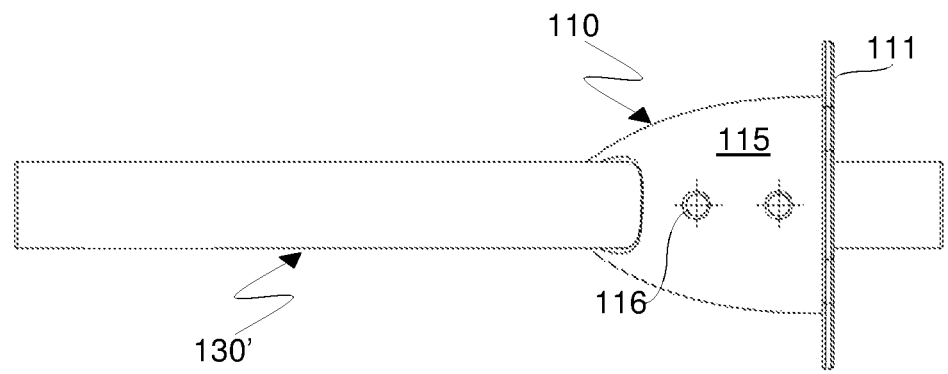
Figure 10:
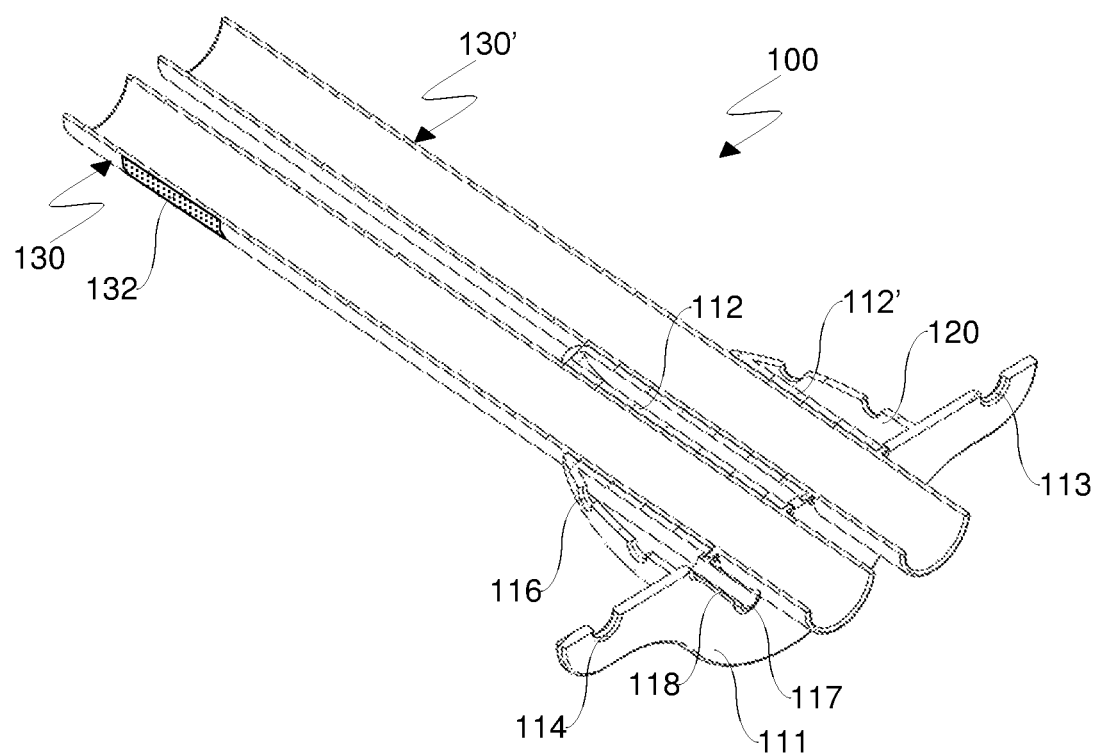
FIG. 10 is a perspective view in longitudinal section of the instrument for accessing and visualizing hollow organs according to the variant shown in the FIGS. 8 and 9.

Referring now to FIGS. 8 to 10, according to a variant of the invention the mouthpiece 110 of the instrument 100 for accessing and visualizing hollow organs may comprise a pair of sleeves 112, 112', for example arranged parallelly through the suction chamber 120 with the corresponding tubular flexible elements 130, 130'. This embodiment of the invention allows the introduction through the instrument 100 of flexible tubular elements 130, 130' both in the digestive tract and in the respiratory tract of a patient and therefore for example the performance of esophagus-gastro-duodenoscopy operations under general anesthesia, where the same instrument 100 is used for the introduction and guiding of endoscopes using one of the two flexible tubular elements 130 and also for patient ventilation using a flexible tubular element 130' with the radially expanding distal end 132.

The present invention has been described hereinabove with reference to preferred embodiments. It is to be understood that other embodiments may exist which belong to the same inventive core, as defined by the scope of the protection of the claims set forth below.

The invention claimed is:

1. An instrument for accessing and visualizing hollow organs, said instrument comprising a mouthpiece configured to be fitted in the mouth of a patient, said mouthpiece comprising a perforated mask and a sleeve having a generally cylindrical or ovoid shape extending from said perforated mask substantially perpendicularly thereto and defining a channel suitable for allowing the introduction of a flexible tubular element, which instrument further comprises sucking means suitable to suck saliva and other fluids from the oral cavity of the patient, said sucking means comprising a suction chamber, or closed volume, that is restrained to the mask on the side where said sleeve is formed, said suction chamber comprising a plurality of through openings adapted to allow fluid communication with a surrounding environment, an intake opening communicating with the suction chamber being formed on the mask, wherein the instrument comprises a dome-shaped member which delimits the suction chamber and in that said through openings are formed on a skirt of the dome-shaped member.

2. The instrument according to claim 1, the flexible tubular element is coaxially fitted in the sleeve or configured to be fitted therein and configured to be anchored to the mouthpiece by way of a locking system, said flexible tubular element having a portion protruding beyond a distal end of the sleeve.

3. The instrument according to claim 1, further comprising an introducing mandrel configured to be coaxially inserted into the flexible tubular element, said introducing mandrel comprising tie rods associated with respective handpieces configured to allow flexion and extension of the introducing mandrel.

4. The instrument according to claim 1, wherein the suction chamber is formed coaxially to the sleeve of the mouthpiece.

5. The instrument according to claim 1, wherein the dome-shaped member comprises a base connected to the mask and a top connected to a free end of the sleeve, which ends at said top.

6. The instrument according to claim 1, wherein at least two of the plurality of through openings are arranged on the dome-shaped member in opposite positions with respect to the sleeve.

7. The instrument according to claim 1, wherein the dome-shaped member has substantially elliptical cross-sections which become larger toward the mask.

8. The instrument according to claim 7, wherein the plurality of through openings are arranged along major axes of substantially elliptical cross-sections of the dome-shaped member.

9. The instrument according to claim 1, wherein the flexible tubular element is removably fitted in the sleeve of the mouthpiece.

10. The instrument according to claim 1, wherein an introducing mandrel and/or the tubular element comprise an endoscopic vision system.

11. The instrument according to claim 1, wherein the flexible tubular element comprises a radially expandable distal portion.

12. The instrument according to claim 1, further comprising a flexible guide configured to be fitted into the flexible tubular element after removing an introducing mandrel, said flexible guide being longer than the flexible tubular element and comprising a plurality of lumens formed in an axial direction so as to allow passage of endoscopes and surgical instruments.

13. An instrument for accessing and visualizing hollow organs, said instrument comprising a mouthpiece configured to be fitted in the mouth of a patient, said mouthpiece comprising a perforated mask and a pair of sleeves, each sleeve having a generally cylindrical or ovoid shape extending from said perforated mask substantially perpendicularly thereto and defining a channel suitable for allowing the introduction of a corresponding flexible tubular element, which instrument further comprises sucking means suitable to suck saliva and other fluids from the oral cavity of the patient, said sucking means comprising a suction chamber, or closed volume, that is restrained to the mask on the side where said sleeve is formed, said suction chamber comprising a plurality of through openings adapted to allow fluid communication with a surrounding environment, an intake opening communicating with the suction chamber being formed on the mask wherein the instrument comprises a dome-shaped member which delimits the suction chamber and in that said through openings are formed on a skirt of a the dome-shaped member.

14. The instrument according to claim 13, wherein said sleeves are arranged parallel to one another through the suction chamber.

15. The instrument according to claim 13, wherein one of said flexible tubular elements comprises a radially expandable distal portion.

* * * * *